United States Patent [19]

Hanselmann

[11] Patent Number: 5,159,100

[45] Date of Patent: Oct. 27, 1992

[54] PROCESS FOR THE PRODUCTION OF CYCLOPROPANENITRILE DERIVATIVES

[75] Inventor: Paul Hanselmann, Visp, Switzerland

[73] Assignee: Lonza Ltd., Gampel/Valais, Switzerland

[21] Appl. No.: 806,211

[22] Filed: Dec. 13, 1991

[30] Foreign Application Priority Data

Dec. 19, 1990 [CH] Switzerland ............... 4029/90

[51] Int. Cl.$^5$ .................. C07C 253/00; C07C 255/46
[52] U.S. Cl. ..................................... 558/347; 558/384
[58] Field of Search ............................... 558/347, 384

[56] References Cited

U.S. PATENT DOCUMENTS 4,203,918  5/1980  Brown ......................... 558/384
4,217,300  8/1980  Lantzsch ................... 558/384 X
4,401,601  8/1983  Martel et al. .............. 558/384 X

FOREIGN PATENT DOCUMENTS 0048301   3/1982  European Pat. Off.
0093511  11/1983  European Pat. Off.
44-28290 11/1969  Japan ........................... 558/347

OTHER PUBLICATIONS

Nelson et al., J. Am. Chem. Soc., vol. 79, (1957), pp. 3467 to 3469.
Harnden, M.R., and Jarvest, R. L., Tetrahedron Letters, vol. 26, (1985), pp. 4265 to 4268.

Primary Examiner—Joseph Paul Brust
Attorney, Agent, or Firm—Fisher, Christen & Sabol

[57] ABSTRACT

A process for the production of cyclopropanenitrile derivatives. A diol of the formula:

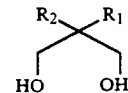

wherein $R_1$ and $R_2$ are the same or different and each is a hydrogen atom, a $C_1$-$C_6$ alkyl group, branched or unbranched, or a $C_1$-$C_6$ alkenyl group, branched or unbranched, or wherein $R_1$ and $R_2$ together is a $C_4$-$C_6$ cycloalkyl ring, is converted with thionyl chloride to a compound of the formula:

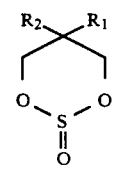

The latter compound is then oxidized to a compound of the formula:

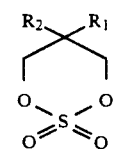

The formula IV compound is converted with a cyano compound to the end product of the formula:

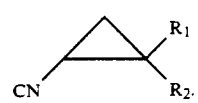

11 Claims, No Drawings

PROCESS FOR THE PRODUCTION OF CYCLOPROPANENITRILE DERIVATIVES

BACKGROUND OF THE INVENTION

1. Field of the Invention

The invention relates to a process for the production of cyclopropanenitrile derivatives.

2. Background Art 2,2-Dimethylcyclopropanenitrile is an important intermediate product for the production of S-(+)-2,2-dimethylcyclopropanecarboxamide. The former compound is hydrolyzed to R,S-2,2-dimethylcyclopropanecarboxylic acid, the acid is converted by resolution of the racemates to the optically pure S-(+)-enantiomer, and the S-(+)-enantiomer is subsequently converted via acid chloride to S-(+)-2,2-dimethylcyclopropane-carboxamide (European Published Patent Application No. 093511). S-(+)-2,2-dimethylcyclopropanecarboxamide is used in turn as the initial material for the production of the dehydropeptidase inhibitor cilastatin, which in treatment is administered together with penem or carbapenem antibiotics to prevent the deactivation of the antibiotics by a renal dehydropeptidase in the kidneys (European Published Patent Application No. 048301).

Nelson et al., J. Am. Chem. Soc., Vol. 79, (1957), pages 3467 to 3469, describes a process for the production of 2,2-dialkylcyclopropanenitriles starting from 2,2-dialkyl-1,3-propanediols. The latter are converted with p-toluenesulfonyl chloride to the ditosylate derivatives and then are reacted with potassium cyanide to the 2,2-dialkylcyclopropanenitriles. A great drawback of this process is that large amounts of potassium tosylate accumulate for disposal as a waste product.

BROAD DESCRIPTION OF THE INVENTION

The main object of the invention is to eliminate the above-described drawbacks and to make available an ecologically and economically feasible process for the production of cyclopropanenitrile derivatives. Other objects and advantages of the invention are set out herein or are obvious herefrom to one skilled in the art.

The objects and advantages of the invention are achieved by the process and compounds of the invention.

The invention involves a process for the production of cyclopropanenitrile derivatives of the formula:

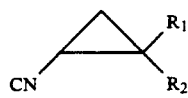
I wherein $R_1$ and $R_2$ are the same or different and each is a hydrogen atom, a $C_1$-$C_6$ alkyl group, branched or unbranched, or $C_1$-$C_6$ alkenyl group, branched or unbranched, or wherein $R_1$ and $R_2$ together is a $C_4$-$C_6$ cycloalkyl ring, is performed so that in the first stage, a diol of the formula:

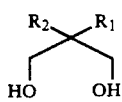
II wherein $R_1$ and $R_2$ have the above meaning, is reacted with thionyl chloride to a compound of the formula:

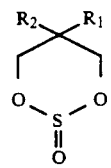
III wherein $R_1$ and $R_2$ have the above meaning, the compound of formula III is oxidized in the second stage to a compound of the formula:

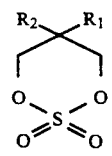
IV wherein $R_1$ and $R_2$ have the same meaning, and the compound of formula IV is converted in the third stage with a cyano compound to the end product.

Preferably the reaction in the first stage is performed with 2,2-dimethyl-1,3-propanediol. Preferably the reaction in the first stage is performed with 1 to 3 mol of thionyl chloride, relative to 1 mol of diol, at a temperature of −10° to 80° C. Preferably the oxidation in the second stage is performed either with an alkali permanganate or with an alkali or alkaline-earth hypochlorite at a temperature of 0° to 80° C. Preferably the reaction in the reaction is performed with an alkali or alkaline-earth hypochlorite in the presence of a catalyst. Preferably the reaction in the third stage takes place with an alkali cyanide at a temperature between 80° and 300° C. Preferably the reaction in the third stage takes place with alkali cyanide in the presence of a base. Preferably in the third stage an alkali carbonate or an alkali bicarbonate is used as a base. Preferably the process is performed without isolating the intermediate stages.

The invention also includes cyclopropanenitrile derivatives of the formula:

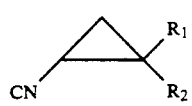
I wherein $R_1$ and $R_2$ together is a $C_4$-$C_6$ cycloalkyl ring. Preferably the cyclopropanenitrile derviative of formula I is 1-cyanospiro[4,2]heptane.

DETAILED DESCRIPTION OF THE INVENTION

The feedstocks, the diols of formula II, can be produced, for example, by alkylation of malonic acid ester derivatives and subsequent reduction to the diol [Harndem, M. R. and Jarvest, R. L., Tetrahedron Letters, (1985), page 4265].

Suitably, the process is performed starting from 2,2-dimethyl-1,3-propanediol. Suitably, the reaction in the first stage is performed with 1 to 3 mol of thionyl chloride, preferably with 1 to 1.5 mol of thionyl chloride, relative to 1 mol of diol of formula II. The reaction in the first stage is performed suitably at a temperature of −10° to 80° C., preferably 20° to 30° C. The reaction in the first stage can be performed with or without solvent. As a solvent, alkanes such as hexane, aromatic hydrocarbons such as toluene, halogenated hydrocarbons such as chloroform, dichloroethane or methylene chloride, tetrahydrofuran or dioxane, preferably toluene, methylene chloride or dichloroethane, can be used in the first stage. The reaction in the first stage takes place usually in a period of 10 minutes to 24 hours, preferably 1 to 2 hours. The product according to formula III optionally can be isolated according to working-up methods usual to one skilled in the art, such as, by washing neutral or distillation. Suitably, the reaction in the second stage takes place without isolating the intermediate product according to formula III.

The oxidation in the second stage can be performed either with an alkali permanganate, a peracid, an alkali chlorate or an alkaline-earth hypochlorite or with an alkali hypochlorite. As the alkali permanganate, for example, potassium permanganate or sodium permanganate can be used. As the peracid, for example, meta-chloroperbenzoic acid can be used. As the alkali chlorate, for example, sodium chlorate or potassium chlorate can be used. As the alkaline-earth hypochlorite, for example, calcium hypochlorite or magnesium hypochlorite can be used. As the alkali hypochlorite, for example, sodium hypochlorite or potassium hypochlorite can be used. Suitably, the oxidation in the second stage takes place either with an alkali permanganate or with an alkali or alkaline-earth hypochlorite. The oxidizing agent is suitably used in an amount of 1 to 3 mol, preferably with 1 to 2 mol, relative to 1 mol of compound of formula III.

The oxidation with an alkali permanganate takes place suitably in the presence of an acid. As the acids, for example, acetic acid or mineral acids, such as, sulfuric acid or hydrochloric acid, can be used. Suitably, the acid is used in excess, relative to the compound of formula III. Preferably, the acid is used in an amount of 2 to 4 mol, preferably 3 mol, relative to 1 mol of the compound of formula III.

The oxidation with an alkali or alkaline-earth hypochlorite takes place suitably in the presence of a catalyst. As the catalyst, for example, a ruthenium compound, an iron compound, a manganese compound, a tungsten compound or a chromium compound can be used. Suitably, a ruthenium trihalide, such as, ruthenium trichloride, ruthenium tribromide or ruthenium triiodide, is used as the catalyst. As the catalyst, a ruthenium-oxygen compound, such as, ruthenium dioxide or ruthenium tetroxide can also be used. Preferably, ruthenium trichloride or ruthenium dioxide is used. Suitably, the catalyst in the second stage is used in an amount of 10 to 0.00001 mol percent, preferably 0.1 to 0.001 mol percent.

As a solvent, hydrocarbons, halogenated for the oxidation stage, such as, methylene chloride or 1,2-dichloroethane, esters, such as, ethyl acetate, ethers, such as, diethyl ether, acetonitrile or aromatic hydrocarbons, such as, for example, toluene, can be used. Preferably, ethyl acetate, methylene chloride or toluene is used as the solvent.

The oxidation in the second stage takes place suitably at a temperature of 0° to 80° C., preferably 20° to 30° C. After a usual reaction time of 0.5 to 24 hours, preferably 3 to 6 hours, the product according to formula IV can optionally be isolated according to working-up methods usual to one skilled in the art, for example, by crystallization, preferably the product according to formula IV is isolated.

The reaction in the third stage takes place with a cyano compound. As the cyano compound, for example, an alkali cyanide can be used. As the alkali cyanide, for example, sodium cyanide or potassium cyanide is used. The cyano compound is suitably used in an amount of 1 to 3 mol, preferably 1 to 2 mol, relative to 1 mol of the compound of formula IV.

Suitably, the reaction in the third stage takes place with an alkali cyanide in the presence of a base. As the base, for example, an alkali carbonate or an alkali bicarbonate can be used. As the alkali carbonate, for example, sodium carbonate or potassium carbonate can be used. As the alkali bicarbonate, sodium bicarbonate or potassium bicarbonate can be used. The base is suitably used in an amount of 1 to 2 mol, relative to 1 mol of alkali cyanide.

Suitably, the reaction in the third stage is performed in a polar solvent, such as, in glycol derivatives, for example, ethylene glycol, diethylene glycol, ethylene glycol monomethyl ether, ethylene glycol monoethyl ether, diethylene glycol monomethyl ether or diethylene glycol monoethyl ether. Preferably, ethylene glycol is used. The reaction in the third stage can also be performed in dimethyl sulfoxide as a solvent under pressure.

Suitably, the reaction in the third stage is performed at a temperature of 80° to 300° C., preferably at 180° to 220° C. After a usual reaction time of 1 to 24 hours, preferably 2 to 5 hours, the end product according to formula I can be isolated according to working-up methods usual to one skilled in the art, e.g., by distillation.

Preferably, the process according to the invention is performed as a one-pot process, and optionally the intermediate product is isolated according to formula IV.

The cyclopropanenitrile derivatives of the formula:

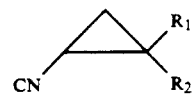

wherein $R_1$ and $R_2$ together is a $C_4$–$C_6$ cycloalkyl ring, are new and can be hydrolyzed to the corresponding $C_4$–$C_6$ cycloalkylpropane-carboxylic acid. A preferred representative of these derivatives is 1-cyanospiro[4,2-]heptane, wherein $R_1$ and $R_2$ together is a $C_5$ cycloalkyl ring.

According to the invention, an ecological and in particular, an inexpensive, economical process for the production of cyclopropanenitrile derivatives is made available. The salts accumulating in this case, for example, sodium or potassium sulfate, can be disposed of as potassium tosylate significantly more easily in contrast to the process described by Nelson et al., J. Am. Chem. Soc., Vol. 79, (1957), pages 3467 to 3469.

EXAMPLE 1

Production of 5.5-dimethyl -1,3,2-dioxathiane-2-oxide 25.36 g (0.24 mol) of 2,2-dimethylpropane-1,3-diol was suspended at room temperature in 150 ml of methylene chloride in a 500 ml three-necked flask. 37.36 g (0.31 mol) of thionyl chloride was instilled over 30 minutes. After the end of the addition, the reaction solution was held at reflux for 1.5 hours and then cooled to room temperature. 100 ml of water was added to the reaction. The aqueous phase was discarded; the organic phase was extracted three times with saturated NaHCO$_3$ solution (100 ml), then dried with Na$_2$SO$_4$ and concentrated by evaporation on a rotary evaporator. The residue was distilled at 24 mbars and 78° C. The product was a pure colorless liquid according to GC and weighed 23.4 g, which corresponded to a yield of 92 percent.

EXAMPLE 2

Production of 5,5-dimethyl-1,3,2-dioxathiane-2,2-dioxide (a) with potassium permanganate:

5 g (0.03 mol) of 5,5-dimethyl-1,3,2-dioxathiene-2-oxide in 100 ml of methylene chloride was introduced in a 250 ml three-necked flask. 100 ml of water and 8.22 g (0.08 mol) of concentrated sulfuric acid were instilled in it. Then, 5.22 g (0.03 mol) of potassium permanganate was slowly added in portions. The reaction suspension was stirred overnight at 30° C., and then the phases were filtered. The organic phase was extracted three times with saturated NaHCO$_3$ solution (100 ml), and then dried and concentrated by evaporation. The crystals were filtered off from the residue and washed with hexane. The product had a melting point of 71° to 74° C. and weighed 2.92 g, which corresponded to a yield of 58 percent.

(b) with sodium hypochlorite:

10.0 g (0.064 mol) of 5,5-dimethyl-1,3,2-dioxathiane-2-oxide was introduced at 20° C. in 100 ml of methylene chloride and 50 ml of water in a 250 ml three-necked flask. 0.02 g of 90 percent ruthenium trichloride was added as a catalyst. 152.45 g (0.0727 mol) of sodium hypochlorite in water was added with stirring for 20 minutes, and the temperature increased to 30° C. The reaction mixture was stirred for five more hours and mixed with 10 drops of isopropanol; the yellow color faded and a black precipitate formed. The water phase was extracted twice with methylene chloride (50 ml), and the combined organic phases were extracted with NaHCO$_3$ solution (100 ml), dried with Na$_2$SO$_4$ and concentrated by evaporation. The white crystalline product was dried overnight at room temperature at a pressure of 15 mbars and weighed 10.65 g, which corresponded to a yield of 99 percent, relative to the 5,5-dimethyl-1,3,2-dioxathiane-2-oxide used.

EXAMPLE 3

Production of 2,2-dimethylcyclopropanenitrile (a) with potassium cyanide:

78 g of ethylene glycol, 5 g (28.6 mmol) of 5,5-dimethyl-1,3,2-dioxathiane-2,2-dioxide and 4.74 g (71.3 mmol) of potassium cyanide were introduced into a 200 ml two-necked flask at room temperature. The reaction suspension was heated to 200° C. and held at this temperature until half of the ethylene glycol was distilled off. The distillate (ethylene glycol and product) was extracted three times with pentane (50 ml) and the combined pentane phases were concentrated by evaporation at standard pressure. The residue was 2.0 g and contained 2,2-dimethylcyclopropanenitrile according to GC. The yield, thus, was 67 percent, relative to 5,5-dimethyl-1,3,2-dioxathiane-2,2-dioxide. For final purification, the product was distilled on the water jet vacuum (boiling point: approximately 45° C., 30 mbars).

(b) with sodium cyanide:

100 g (0.590 mol) of 5,5-dimethyl-1,3,2-dioxathiene-2,2-dioxide and 75 g (1.504 mol) of sodium cyanide were introduced in 750 ml (834.8 g, 13.449 mol) of ethylene glycol in a 1000 ml two-necked flask. The reaction suspension was brought to a temperature of 220° C. over 1.5 hours, and a mixture of ethylene glycol and product was distilled off. It was distilled until half of the ethylene glycol (400 ml) was in the receiver. The contents of the receiver were again distilled at 30° C. and 150 mbars. The product weighed 61.3 g and contained about 10 percent water according to GC. Thus, the yield is about 90 percent, relative to 5,5-dimethyl-1,3,2-dioxathiane-2,2-dioxide.

EXAMPLE 4

Production of 5,5-dimethyl-1,3,2-dioxathiane-2,2-oxide

One-pot process:

(a) with sodium hypochlorite:

100.1 g (0.942 mol) of 98 percent 2,2-dimethyl-1,3-propanediol was introduced in a 1.5 liter three-necked flask at room temperature and mixed with 113.6 g (0.952 mol) of 99.5 percent thionyl chloride with stirring. A strong gas generation took place; at the same time the temperature dropped from room temperature to 5° C. and a solution resulted. After 1 hour, 300 ml of ethyl acetate was added and the ethyl acetate solution was extracted twice with saturated NaHCO$_3$, solution (150 ml). The aqueous phase was discarded. 0.02 g (0.0001 mol) of 90 percent ruthenium trichloride was added to the organic phase and then 1078 g (1.5 mol) of a 10.5 percent aqueous sodium hypochlorite solution was instilled for 1 hour. In so doing, the reaction temperature increased up to the boiling point of the ethyl acetate. After the end of the addition, the reaction was allowed to stand overnight and then mixed with 5 ml of isopropanol. The black catalyst was filtered off and the phases were separated. The organic phase was dried with Na$_2$SO$_4$ and concentrated by evaporation on a rotary evaporator at 35° C. and 90 mbars. After the removal of 50 percent of the ethyl acetate, the product began to precipitate. The resulting suspension was put in an ice bath and the precipitated white crystals were filtered off. Then the precipitate was dried at 50° C. and 50 mbars overnight in a drying oven. The product weighed 90.9 g and had a melting point of 80° C. The mother liquor was totally concentrated by evaporation and, after drying, again yielded 32.2 g with a melting point of 78° C. The yield in pure product, thus, was 78 percent, relative to the 2,2-dimethyl-1,3-propanediol used.

(b) with calcium hypochlorite:

31.0 g (0.289 mol) of 100 percent 2,2-dimethyl-1,3-propanediol was suspended at room temperature in 185 ml of toluene in a 500 ml three-necked flask. Then, 34.9 g (0.294 mol) of 99.5 percent thionyl chloride was instilled, and a gas generation took place. The reaction was held between 20° to 30° C. first by heating and then by cooling. After the end of the addition of thionyl chloride, all of the propanediol was dissolved. The toluene phase was washed with 50 ml of saturated Na$_2$CO$_3$ solution. 0.006 g ($3.8 \times 10^{-5}$ mol) of 90 percent ruthenium trichloride and 200 ml of water were added to the organic phase. With vigorous stirring, 43.7 g (0.206 mol) of 67.5 percent calcium hypochlorite was now sprinkled in. The temperature of the reaction was held at 25° to 30° C. by cooling. The resultant white suspension/emulsion was mixed with 5.7 ml (6.7 g, 0.067 mol) of 37 percent HCl and two clear phases were formed, which were separated. The toluene phase was dried with Na$_2$SO$_4$ and evaporated to dryness on a rotary evaporator. The residue weighed 40.6 g and consisted of up to 98.1 percent by weight of the desired product. The yield was 81 percent, relative to the 2,2-dimethyl-1,3-propanediol used.

EXAMPLE 5

Production of 2,2-dimethycyclopropanenitrile with sodium cyanide and sodium carbonate as a base 1000 ml (556 g, 8.966 mol) of ethylene glycol with 49.9 g (0.300 mol) of 5,5-dimethyl-1,3,2-dioxathiane-2,2-dioxide, 15 g (0.306 mol) of sodium cyanide and 31.8 g (0.300 mol) of sodium carbonate were introduced in a 500 ml two-necked flask at room temperature. The reaction suspension was heated to 220° C. over 1.5 hours, and a mixture of the product and ethylene glycol was distilled off. The distillation was continued until no more ethylene glycol was distilled off. The receiver (504 g) was distilled again at 90° C. and 150 mbars, and 21.78 g of product was obtained. Thus, the yield was 67 percent, relative to the 5,5-dimethyl-1,3,2-dioxathiane-2,2-dioxide used.

EXAMPLE 6

Production of 1-cyanospiro[4,21]heptane 1.27 g (0.026 mol) of sodium cyanide and 5.55 g (0.026 mol) of 3,5,4-dioxathiaspiro[4,5]decane-4,4-dioxide were suspended at room temperature in 40 ml of ethylene glycol and heated for 15 minutes to 150° C. Then, the reaction was allowed to cool to 80° C. and 5.5 g (0.052 mol) of Na$_2$CO$_3$ (anhydrous) was added. 22.3 g of ethylene glycol was distilled off over a simple distillation bridge, at a bath temperature of 225° C. The distillate contained about 1 percent of the spiro compound, which was identified, based on its MS spectrum, in particular its typical (M−1)$^+$, of 120.

What is claimed is:

1. Process for the production of a cyclopropanenitrile derivative of the formula:

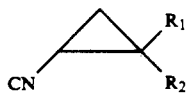
I wherein R$_1$ and R$_2$ are the same or different and each is a hydrogen atom, a C$_1$-C$_6$alkyl group, branched or unbranched, or a C$_1$-C$_6$ alkenyl group, branched or unbranched, or wherein R$_1$ and R$_2$ together are a C$_4$-C$_6$ cycloalkyl ring, characterized in that, in a first stage, a diol of the formula:

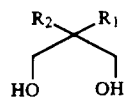
II wherein R$_1$ and R$_2$ have the above-mentioned meaning, is reacted with thionyl chloride to a compound of the formula:

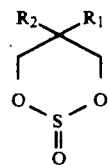
III wherein R$_1$ and R$_2$ have the above-mentioned meaning, in the second stage, the compound of formula III is oxidized to a compound of the formula:

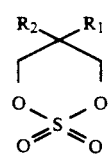
IV wherein R$_1$ and R$_2$ have the above-mentioned meaning, and, in the third stage, the compound of formula IV is converted with a cyano compound to the cyclopropanenitrile derivative of formula I.

2. Process according to claim 1 wherein the reaction, in the first stage, is performed with 2,2-dimethyl-1,3-propanediol.

3. Process according to claim 2 wherein the reaction, in the first stage, is performed with 1 to 3 mol of thionyl chloride, relative to 1 mol of the diol of formula II, at a temperature of −10° to 80° C.

4. Process according to claim 1 wherein the oxidation in the second stage, is performed either with an alkali permanganate or with an alkali or alkaline-earth hypochlorite at a temperature of 0° to 80° C.

5. Process according to claim 4 wherein the reaction is performed with an alkali or alkaline-earth hypochlorite in the presence of a catalyst.

6. Process according to claim 1 wherein the reaction, in the third stage, takes place with an alkali cyanide at a temperature between 80° and 300° C.

7. Process according to claim 6 wherein the reaction takes place with alkali cyanide in the presence of a base.

8. Process according to claim 7 wherein an alkali carbonate or an alkali bicarbonate is used as the base.

9. Process according to claim 8 wherein the process is performed without isolating the intermediate stages.

10. Process according to claim 1 wherein the reaction, in the first stage, is performed with 1 to 3 mol of thionyl chloride, relative to 1 mol of the diol of formula II, at a temperature of −10° to 80° C.

11. Process according to claim 1 wherein the process is performed without isolating the intermediate stages.

* * * * *